United States Patent
Ring et al.

(10) Patent No.: US 6,824,794 B2
(45) Date of Patent: Nov. 30, 2004

(54) METHOD AND APPARATUS FOR PREVENTING BACTERIA AND ALGAE GROWTH IN WATER

(75) Inventors: Terry A. Ring, Salt Lake City, UT (US); Tom Smolkov, Holliday, UT (US); M. Anthony Gamarra, Murray, UT (US)

(73) Assignee: Innovative Water Technologies, Inc., Murray, UT (US)

( * ) Notice: Subject to any disclaimer, the term of this patent is extended or adjusted under 35 U.S.C. 154(b) by 0 days.

(21) Appl. No.: 10/159,135

(22) Filed: May 31, 2002

(65) Prior Publication Data

US 2003/0022793 A1 Jan. 30, 2003

Related U.S. Application Data

(60) Provisional application No. 60/295,174, filed on Jun. 1, 2001.

(51) Int. Cl.$^7$ .................. A01N 59/20; A01N 59/02; A01N 59/26; A01N 37/44; C02F 1/50

(52) U.S. Cl. .................. 424/638; 424/601; 424/602; 424/604; 424/605; 424/606; 424/613; 424/614; 424/615; 424/616; 424/618; 424/619; 424/637; 424/666; 424/713; 424/718; 424/722; 424/DIG. 6; 514/108; 514/566; 514/574; 514/714; 514/970; 422/28; 210/758; 210/759; 210/764; 504/151; 504/152

(58) Field of Search .................. 424/601–602, 424/604–606, 613–616, 618–619, 637–638, 666, 713, 718, 722, DIG. 6; 514/108, 566, 574, 714, 970; 422/28; 210/758, 759, 764; 504/151, 152

(56) References Cited

U.S. PATENT DOCUMENTS

| | | | | |
|---|---|---|---|---|
| 3,329,607 A | * | 7/1967 | Colobert et al. | 210/758 |
| 3,617,576 A | * | 11/1971 | Kerst | 210/699 |
| 4,361,435 A | | 11/1982 | Meyers et al. | |
| 4,512,900 A | * | 4/1985 | Macur et al. | 588/225 |
| 5,149,354 A | | 9/1992 | Delaney | |
| 5,449,658 A | | 9/1995 | Unhoch et al. | |
| 5,541,150 A | | 7/1996 | Garris | |
| 5,700,377 A | | 12/1997 | Cox | |
| 5,780,064 A | * | 7/1998 | Meisters et al. | 424/616 |
| 5,955,486 A | * | 9/1999 | Mattox | 514/372 |
| 6,093,422 A | | 7/2000 | Denkewicz, Jr. et al. | |
| 6,120,698 A | * | 9/2000 | Rounds et al. | 252/181 |
| 6,149,821 A | * | 11/2000 | Rounds et al. | 210/754 |

FOREIGN PATENT DOCUMENTS

WO 99/59924 * 11/1999

* cited by examiner

Primary Examiner—John Pak
(74) Attorney, Agent, or Firm—TraskBritt

(57) ABSTRACT

A water treatment agent and method of treating water to inhibit, reduce, or prevent the formation of algae and bacteria in a water body. The water treatment agent may include copper sulfate penta-hydrate and/or silver, di-sodium ethylene di-amine tetra-acetic acid dihydrate, a scale inhibitor, a shocking agent and a buffer agent. For instance, the treatment agent may include a composition of copper sulfate pentahydrate, di-sodium ethylene di-amine tetra-acetic acid, monopotassium phosphate or sulfuric acid, and potassium monopersulfate and 1-hydroxyethylidene-1,1-diphosphonic acid.

30 Claims, No Drawings

METHOD AND APPARATUS FOR PREVENTING BACTERIA AND ALGAE GROWTH IN WATER

REFERENCE TO RELATED APPLICATION

This application claims the benefit of U.S. Provisional application No. 60/295,174, filed Jun. 1, 2001.

BACKGROUND OF THE INVENTION

Field of the Invention: The present invention relates to a chemical composition to be added to water, such as in swimming pools, spas, hot tubs, industrial processes, or other water bodies to inhibit, reduce, or prevent the growth of bacteria and/or algae and the formation of common scale minerals in the water.

State of the Art: Many different types of algicides and bacteriacides, also known as treatment agents, have been used to treat water to prevent the growth of algae and bacteria. Use of such treatment agents is especially prevalent in circulating water systems, such as those found in swimming pools, spas, hot tubs, and industrial processes. In addition to preventing the growth of algae and bacteria in water, treatment agents are sometimes used to enhance the aesthetic appeal of the water being treated.

Many recreational water bodies, such as swimming pools, hot tubs, and spas, are susceptible to the formation and growth of algae and bacteria if improperly treated. In addition, the water used to create such water bodies is often hard water, susceptible to scaling, precipitation, and clouding. For example, most swimming pools and hot tubs are filled with tap water drawn from a well or city water supply. Such water typically contains dissolved metals, such as iron, and other impurities, such as calcium carbonate. As water from the water body evaporates, additional tap water is added to replace the lost water. This leads to the concentration of the metals and impurities in the water body. Eventually, the concentration of the metals and impurities results in the formation of scale on surfaces contacting the concentrated water or precipitation of the impurities from the water body. For example, as dissolved calcium carbonate concentrations in a water body are increased by evaporation and refilling, the calcium carbonate begins to precipitate. Calcium carbonate precipitate typically forms as scale on the surfaces holding the water body. Scale formation may be more prevalent on heat transfer surfaces where temperature increases precipitation. The formation of scale, besides being unsightly, is unwanted because it ruins equipment and increases maintenance costs for maintaining controlled water bodies.

To prevent algae blooms, scaling and unwanted precipitation, water bodies are treated. Some of the best-known treatment agents are chlorine and bromine based treatment agents. However, the chlorine and bromine based treatment agents frequently cause skin and eye irritation and are easily recognized by their unpleasant smell. Furthermore, chlorine and bromine react with organic matter in the water to produce foul smelling chloramines and trihalomethanes. In animal toxicological studies with high doses of trihalomethanes an increase in the occurrence of some cancers was observed, which convinced the United States Environmental Protection Agency (EPA) to set limits and regulate human exposure to them. To avoid the irritation and smell of chlorine and bromine based treatment agents, many alternative non-chlorine and non-bromine based treatment agents have been developed. For example, BAQUACIL®, a product of Zeneca, Inc., is a well-known treatment agent used in swimming pools, spas, and hot tubs. BAQUACIL's®) unique composition of poly hexamethylenebiguanide (PHMB) provides a substantially irritation free and odorless treatment agent preferable to chlorine for treating swimming pools. Another example of a well-known treatment agent used as the primary ingredient in several commercial products used in swimming pools, spas, and hot tubs is Oxone®, a product by DuPont, Inc. Oxone's active ingredient is potassium peroxymonosulfate, commonly known as potassium nionopersulfate, an agent also known as a non-chlorine shock. Potassium monopersulfate, like chlorine and bromine is an oxidizing agent that chemically breaks down organic matter in the water, preventing the formation of toxic trihalomethanes.

Many other chemical compositions are also available for treating water. For example, heavy metal ions such as copper, silver, zinc, tin, and nickel have each been used as water treatment agents. The metal ions may be generated in a water supply using electrolysis or by the addition of the metal ion in a solid or liquid form. For example, copper ions are commonly introduced to water as treatment agents in the form of copper sulfate, copper acetate, copper chloride, copper formate, and copper carbonate. One of the problems associated with the use of copper, however, is the tendency of copper ions to react with naturally occurring anions in the water and to precipitate as insoluble salts. To help prevent precipitation, sequestering or chelating agents have been used to enhance the stability of the copper ions in solution. One such chelating agent is ethylene diamine tetra acetic acid (EDTA). The EDTA chelates with the copper ions, or other metal ions, to help prevent precipitation of the metal ion and the staining and scaling caused by such precipitation.

The use of copper ions alone to treat water fails to eliminate undesired calcium carbonate scaling and the precipitation of other metals naturally occurring in water. Although a copper ion source may be combined with EDTA to treat water bodies, problems with precipitation continue to exist. Thus, a treatment agent capable of inhibiting or preventing the formation of algae and bacteria in a water body and also capable of eliminating scaling, controlling the clarity of the water, and controlling the pH of the water is desirable.

SUMMARY OF THE INVENTION

The present invention includes a water treatment agent (e.g. composition or mixture) and a method for treating water to inhibit, reduce, or prevent the growth of algae and bacteria, to chemically decompose any organic matter, to inhibit scaling, and to control the pH and clarity of the water.

The treatment agent of the present invention includes copper sulfate penta-hydrate, di-sodium ethylen di-amine tetra-acetric acid dihydrate, a scale inhibitor, and a shocking agent. In addition, a buffering agent may be included in the treatment agent. Scale inhibitors that may be used with the treatment agent of the present invention include 1-hydroxyethylidene-1,1-diphosphonic acid, nitrilo tr(methylene phosphoric)acid, 2-phosphono 1,2,4 butane tri carboxylic acid, $H_5P_3O_{10}$, phosphino poly carboxlic acid, poly acrylic acid, and sulfonated poly acrylic acid. Shocking agents may include monopotassium phosphate, potassium monopersulfate, sodium monopersulfate, alkali monopersulfates, and potassium hydrogen peroxymonosulfate sulfate. Buffering agents may include monopotassium phosphate, sulfuric acid, hydrochloric acid, nitric acid, muriatic acid, and oxalic acid.

In a preferred embodiment, the treatment agent includes a chemical composition or mixture including a concentrated solution of about 5 percent by weight of copper sulfate penta-hydrate ($CuSO_4 \cdot 5H_2O$), about zero to about 2.6 percent by weight di-sodium ethylene di-amine tetra-acetic acid dihydrate ($Na_2EDTA \cdot 2H_2O$), about zero to about 1 percent by weight monopotassium phosphate ($KH_2PO_4$), about zero to about 4.3 percent by weight potassium monopersulfate ($KHSO_5$), and about zero to about 1 percent by weight 1-hydroxyethylidene-1,1-diphosphonic acid (HEDP). The treatment agent may be added to a body of water. Ideally, the amount of the treatment agent added to the water body is sufficient to maintain a copper concentration throughout the water body of approximately 1 ppm, and preferably between about zero and about 1.3 ppm. The treatment agent of the present invention may be periodically added to the water body to maintain the desired copper concentration.

In another embodiment of the present invention, the treatment agent may include a chemical composition or mixture comprising a concentrated solution of copper sulfate penta-hydrate, $Na_2EDTA \cdot 2H_2O$, HEDP, potassium monopersulfate and as much as 15 percent of an acid, such as sulfuric acid ($H_2SO_4$). The treatment agent may be added to a body of water on a periodic basis to treat the water body. Preferably, the sulfuric acid is first used to achieve a desired pH in the water body. Periodic additions of the treatment agent may then be used to inhibit the formation of algae and bacteria, prevent scaling, and maintain the pH of the water and the desired water quality.

DETAILED DESCRIPTION OF THE INVENTION

The present invention relates to the treatment of water. More specifically, the present invention relates to a water treatment agent and a method of adding the treatment agent to water to inhibit, reduce, or prevent the growth of bacteria and/or algae in the water, to chemically degrade dead organic matter, to prevent scaling on surfaces contacted by treated water, to control the pH of the water, and to control the clarity of the water. Preferably, the water treatment agent is formulated as a liquid that can be easily metered into a water body on a periodic basis or with automatic metering equipment.

One embodiment of the treatment agent of the present invention includes a chemical composition or mixture of copper sulfate penta-hydrate ($CuSO_4 \cdot 5H_2O$), monopotassium phosphate ($KH_2PO_4$), disodium ethylene diamine tetra-acetic acid dihydrate ($Na_2EDTA \cdot 2H_2O$), potassium monopersulfate ($KHSO_5$), and 1-hydroxyethylidene-1,1-diphosphonic acid (HEDP). The treatment agent is added to a water body, such as those found in a swimming pool or hot tub, to inhibit, reduce, or prevent the formation of bacteria and/or algae, to chemically degrade dead organic matter, to control the pH of the water, to control the clarity of the water, and to prevent scaling on surfaces contacted by the treated water.

The copper sulfate penta-hydrate in the treatment agent inhibits or prevents the growth of algae and bacteria in the water. It has been found that a concentration of 1 part-per-million (ppm) of copper in the water body is usually sufficient to inhibit, reduce, or prevent the growth of algae and bacteria in the e water body. In addition, this concentration is below the concentration of copper suggested by the EPA for safe drinking water. The total amount of copper sulfate penta-hydrate in a body of treated water depends upon the concentration of the copper sulfate penta-hydrate in the treatment agent added to the water and the amount of treatment agent added to the water. These amounts may vary by water source and by treatment agent batch. Therefore, it is within the scope of this invention to provide a sufficient amount of copper sulfate penta-hydrate in the treatment agent of the present invention to inhibit the growth of algae and/or bacteria in a water supply.

Silver may also be added in conjunction with copper to kill bacteria. In ponds and fountains silver may be used instead of copper to effectively kill bacteria therein. Any soluble form of silver may be used as an additive to the treatment agent for this purpose. For instance, silver in the form of silver nitrate ($AgNO_3$) may be used. Alternatively, particulate forms of silver may be added to the treatment agent of the present invention. The maximum level of silver allowed by the EPA for drinking water is 0.10 mg/liter of silver, thus any use of silver, in a particulate or soluble form, with the treatment agent of the present invention would preferably result in final treated water body concentration having a silver content below this level.

Monopotassium phosphate may be added, in conjunction with the sodium ions that are part of the $Na_2EDTA \cdot 2H_2O$ addition, as a buffering agent to maintain the pH of the treated water. This is especially important where the present invention is used to treat recreational use water bodies such as swimming pools, hot tubs, and spas. The human body is most comfortable in water having a pH between about 5 and 9, and preferably around 7. The pH may be controlled by balancing the addition of a buffering agent with the amount of sodium ions present from the addition of $Na_2EDTA \cdot 2H_2O$ with the treatment agent.

Sulfuric acid may also be added to the treatment agent of the present invention. Addition of a treatment agent containing sulfuric acid, as in the present invention, to a water body may also help maintain the pH of the water body near a pH level best tolerated by humans and helps to prevent hydroxide precipitation. Sulfuric acid may also be added to the concentrated treatment agent to stabilize the concentrated treatment agent formulation against precipitation at low storage temperatures, for example, at temperatures below 0° C.

Furthermore, the addition of sulfuric acid to the water body helps control unwanted precipitation of metals, such as iron, from the water. Metals tend to precipitate more readily in water having a basic pH. For example, iron present in water having a basic pH precipitates as ferric hydroxide. Such precipitation clouds the water, reducing the clarity thereof and forms rust colored stains and scales. The addition of sulfuric acid, as in the present invention, reduces the pH of the water to an acidic level, thereby hindering the precipitation of metals and aiding in the clarification of the treated water. In addition, calcium carbonate precipitates from a basic water body more readily than from an acidic water body. Typically, calcium carbonate precipitates or scales onto surfaces contacted by the water body, and more readily on heat transfer surfaces used to heat the water body or circulate water in the water body. By reducing the pH of the water body with sulfuric acid, calcium carbonate precipitation may be reduced and scaling prevented.

As an alternative to sulfuric acid, the treatment agent of the present invention may include other strong acids, such as HCl and $HNO_3$, or other weak acids such as muratic acid, oxalic acid, and the like as known in the art.

To further reduce the precipitation of iron in a water body treated with the present invention, $Na_2EDTA \cdot 2H_2O$ is added to the treatment agent. It is well known that EDTA is a complexing agent. When mixed with the copper sulfate penta-hydrate of the present invention, the EDTA complexes the copper ion in solution. EDTA complexes better with iron than with copper, however. When the copper/EDTA complex of the present invention is added to a water body, the copper/EDTA complexes are lost in favor of forming iron/EDTA complexes if iron ions are present in the water body. The formation of iron/EDTA complexes prevents the formation and precipitation of iron hydroxides, thereby improving water clarity. The presence of EDTA in the treated water may also reduce the precipitation of calcium in the water. Just as EDTA complexes with iron and copper, EDTA complexes with calcium ions, thereby reducing the precipitation of calcium carbonate in water bodies treated with the chemical composition of the present invention.

In addition to the anti-precipitation benefits of adding EDTA to a water body as part of the treatment agent of the present invention, the presence of EDTA provides an esthetic benefit. The copper/EDTA complex of the present invention produces a blue color in the treatment agent. This blue color is transferred to the water body to which the treatment agent of the present invention is added. Although diluted when added to the treated water, the blue color of the treatment agent helps to make the treated water appear blue. Often times, it is esthetically pleasing to the eye to make recreational water bodies appear blue in color.

Although $Na_2EDTA.2H_2O$ is a preferred complexing agent for the treatment agent of the present invention, other complexants may be used. For example, the acid form of the sodium salt EDTA may be used. Ethylene diamine could substitute for the $Na_2EDTA.2H_2O$ as a stronger copper complexant and to provide a more intense blue color to a treated water body. Even ammonia may be used, although ammonia tends to increase the pH of the water and promote the precipitation of iron from the treated water.

Potassium monopersulfate may be included in the treatment agent of the present invention as a non-chlorine shocking agent to oxidize organic matter in the water. Potassium monopersulfate's oxidizing power also plays a significant role in inhibiting or preventing the growth of algae and bacteria in the water. A large number of dead organisms cause the water to look cloudy. Once the algae and bacteria have been killed, by either the copper or the potassium monopersulfate or its combination, the dead organism is oxidized or digested by potassium monopersulfate to produce organic matter that is clear to the eye. Eventually the organic matter is flocculated and may be trapped by a filter or filter system in a pool, spa, hot tub, or other water body. Other non-chlorine shocks or shocking agents which may also be used with the present invention include other alkali monopersulfates including sodium monopersulfate and the like.

Potassium hydrogen peroxymonosulfate sulfate ($2KHSO_5.KHSO_4.K_2SO_4$) may also be added to the treatment agent as the auxiliary oxidant or shocking agent for the purpose of reducing organic content in water. The potassium peroxymonosulfate ($KHSO_5$), or potassium monopersulfate, content of the potassium hydrogen peroxymonosulfate sulfate may be used in addition to or in place of any added potassium monopersulfate in a treatment agent. If potassium hydrogen peroxymonosulfate sulfate is used with the treatment agent, the amount added to the concentrated treatment agent may be on the order of zero to 120 gm/liter after dilution or zero to 268 gm/liter of potassium hydrogen peroxymonosulfate sulfate in the concentrated form.

The HEDP in the treatment agent of the present invention is used primarily to inhibit hard water scale formation. It has been found that HEDP acts as a calcium carbonate scale inhibitor at concentrations of about 1 to 10 ppm. Therefore, the treatment agent of the present invention may include enough HDEP to raise the HEDP concentration in the treated water to between 1 ppm and 10 ppm. HEDP also acts as an algae growth inhibitor, providing additional treatment qualities to the treatment agent of the present invention.

Other scale inhibitors capable of inhibiting calcium carbonate scaling or other scaling may also be used with the treatment agent of the present invention. For instance, as an alternative, any of the following could be substituted for HEDP in the treatment agent of the present invention: nitrilo tri(methylene phosphoric) acid; 2-phosphono 1,2,4 butane tri carboxylic acid; $H_5P_3O_{10}$; phosphino poly carboxlic acid; poly acrylic acid; or sulfonated poly acrylic acid.

The desired concentrations of each component of the treatment agent may vary depending upon the size and condition of the water body being treated. In a preferred embodiment, a treatment agent for adding to a water body on a periodic basis includes a concentrated solution of copper sulfate penta-hydrate having between about zero to about 31.6 percent by weight copper sulfate penta-hydrate, between about zero and about 15 percent by weight sulfuric acid ($H_2SO_4$), between zero and about 10 percent monopotassium phosphate, between about zero and about 2.6 percent by weight $Na_2EDTA.2H_2O$, and preferably about 2.56 percent by weight $Na_2EDTA.2H_2O$, between zero and about 8.6 percent by weight potassium monopersulfate and between about zero and about one percent by weight HEDP.

In another embodiment, the treatment agent includes a concentrated solution of about 5 percent by weight copper sulfate penta-hydrate mixed with about 4.3 percent by weight potassium monopersulfate, with either about 1 percent monopotassium phosphate, or about 46 grams per liter of sulfuric acid, 0.8 percent by weight $Na_2EDTA$ dihydrate, and between about zero to about one percent by weight HEDP.

The treatment agent of the present invention may be added to a water body on a regular basis to inhibit, reduce, or prevent the formation of bacteria and/or algae in the water body, and to control the pH of the water, the clarity of the water, and to prevent scaling on surfaces in contact with the treated water. Ideally, a sufficient amount of the treatment agent is added to the water body to produce about 1 ppm of copper throughout the water body. The amount of the treatment agent added to a water body, therefore, depends on the size of the water body and the concentration of copper in the treatment agent of the present invention. For example, a hot tub containing about four hundred gallons of water may require the addition of about 30 milliliters of a preferred mixture of the treatment agent per week to treat the hot tub water and maintain a copper level of 1 ppm.

In an alternate embodiment of the present invention, a buffer may be used in place of the sulfuric acid to anchor the pH of a water body within a certain range. The buffer may include any of a number of chemical compositions capable of balancing the pH in a water body. For example, a buffer comprising a weak acid and a salt of the same acid may be used. Alternatively, a buffer comprising a weak base and its salt could also be used. In still another embodiment, a slightly soluble acid or base providing an excess of the substance in a second phase may also be used as a buffer. For best results, a large addition of a buffer agent to a water body is performed before the addition of a treatment agent of the present invention. The addition of the buffer to the water body before treatment stabilizes the pH of the water body at or near the desired pH, allowing the treatment agent to treat the water body and maintain the desired pH level in the water body.

Examples of different buffering agents which may be used with the present invention include: citric acid with di-sodium hydrogen phosphate; acetic acid with sodium acetate; sodium bicarbonate with sodium hydroxide; phthalic acid with potassium hydrogen phthalate; potassium dihydrogen phosphate with dipotassium hydrogen phosphate; or boric acid with sodium borate.

A preferred treatment agent of the present invention using a buffer instead of sulfuric acid includes a chemical composition or mixture having a solution containing about zero and about 31.6 percent by weight copper sulfate penta-hydrate, between about zero and about 2.56 percent by weight $Na_2EDTA$ dihydrate, between zero and about 8.6 percent by weight potassium monopersulfate, between about zero to about one percent by weight HEDP, and between about zero and about 33 percent by weight monopotassium phosphate in combination with between about zero and about 33 percent by weight sodium hydroxide.

Another embodiment of the buffered treatment agent of the present invention includes a concentrated solution of about 5 percent by weight copper sulfate penta-hydrate mixed with about 0.8 percent by weight $Na_2EDTA$ dihydrate, between about zero to about one percent by weight HEDP, between zero and about 8.6 percent by weight potassium monopersulfate, and a buffered product having a pH of about 6.8 after dilution including about 1 percent by weight monopotassium phosphate and about 0.13 percent by weight sodium hydroxide.

Treatment agents formed in accordance with the present invention may also include about 50 gm/liter to about 100 gm/liter copper sulfate penta-hydrate; about 4 gm/liter to about 8 gm/liter di-sodium ethylene di-amine tetra-acetic acid dihydrate; about 5 ml/liter to 10 ml/liter 1-hydroxyethylidene-1,1-diphosphonic acid; and about 10 gm/liter to about 100 gm/liter shocking agent. If monopotassium phosphate is used as a shocking agent, about 10 gm/liter to about 20 gm/liter are preferably used. If potassium monopersulfate is used as a shocking agent, about 50 gm/liter to about 100 gm/liter are preferably used. Silver, in an amount of about zero to about 0.08 gm/liter may also be added to the treatment agent if desired.

Some examples of treatment agent formulations according to the present invention have been tested against the EPA chlorine standard for swimming pools. The formulations of such treatment agents are described in the Examples herein. Data showing the effectiveness of the example formulations at killing *Escherichia Coli*, or *E. Coli*, at various benchmark times are compiled as log reduction values in Tables I and II. Also included in each of the tables is log reduction data for chlorine samples against which treatment agents are considered for approval by the EPA.

The following treatment agent formulations for one liter of treatment agent were formed in accordance with the present invention:

EXAMPLE A 50 gm/liter $CuSO_4 19\ 5H_2O$
8 gm/liter $Na_2EDTA \cdot 2H_2O$
10 gm/liter $KH_2PO_4$
5 ml/liter HEDP

EXAMPLE B 50 gm/liter $CuSO_4 \cdot 5H_2O$
8 gm/liter $Na_2EDTA \cdot 2H_2O$
10 gm/liter $KH_2PO_4$
5 ml/liter HEDP
100 gm/liter $K_2SO_4 \cdot KHSO_4 \cdot 2KHSO_5$

EXAMPLE C 50 gm/liter $CuSO_4 19\ 5H_2O$
8 gm/liter $Na_2EDTA \cdot 2H_2O$
10 gm/liter HEDP
5 ml/liter $K_2SO_4 \cdot KHSO_4 \cdot 2KHSO_5$

EXAMPLE D 50 gm/liter $CuSO_4 19\ 5H_2O$
4 gm/liter $Na_2EDTA \cdot 2H_2O$
10 gm/liter $KH_2PO_4$
5 ml/liter HEDP

EXAMPLE E 100 gm/liter $CuSO_4 19\ 5H_2O$
5 gm/liter $Na_2EDTA \cdot 2H_2O$
10 ml/liter HEDP
20 gm/liter $KH_2PO_4$

EXAMPLE F 50 gm/liter $CuSO_4 19\ 5H_2O$
10 ml/liter HEDP
20 gm/liter $KH_2PO_4$

EXAMPLE G 50 gm/liter $CuSO_4 \cdot 5H_2O$
8 gm/liter $Na_2EDTA \cdot 2H_2O$
10 gm/liter $KH_2PO_4$
5 ml/liter HEDP
0.08 gm/liter $AgNO_3$ Each of the example formulations were tested to determine efficacy of use in water bodies such as swimming pools. In each test case, the treatment agent formulation was diluted to reduce the total parts per million of copper to simulate a treated water body. The results of the tests on formulations A, B, and C are illustrated in Table I and the results of the tests on formulations D, E, F, and G are illustrated in Table II. The method used to test each of the example formulations was the AOAC Official Method 965.13 Disinfectants (Water) for Swimming Pools against *E. coli* ATCC 11229 (*Escherichia. Coli*). The tests resulted in log reduction values corresponding to the amount of *Escherichia Coli* left after exposure to the various example formulations. A log reduction of 3 corresponds to killing 99.9% of the organisms and a log reduction of 6 corresponds to killing 99.9999% of the organisms. A chlorine standard meeting the EPA requirements for swimming pool treatment was also tested. The data from the chlorine standard may be used to compare the effectiveness of the example formulation to the EPA chlorine standards. The results of the tests are summarized in the following Tables:

TABLE I

| SAMPLE | log Reduction Values | | |
|---|---|---|---|
| | 30 seconds | 1 minute | 5 minutes |
| 0.6 ppm Chlorine Standard | 3.2 | 3.3 | 3.5 |
| Example A Formulation diluted to 1.2 ppm Cu | 2.4 | 2.5 | 3.3 |
| Example B Formulation diluted to 1.2 ppm Cu | 0.2 | 1.2 | 2.2 |
| Example C Formulation diluted to 1.2 ppm Cu | 0.2 | 1.2 | 2.2 |

TABLE II

| SAMPLE | log Reduction Values | | |
|---|---|---|---|
| | 30 seconds | 1 minute | 5 minutes |
| 0.6 ppm Chlorine Standard | 6.0 | 6.0 | 6.0 |
| Example D Formulation diluted to 1.2 ppm Cu | 6.0 | 6.0 | 6.0 |
| Example E Formulation diluted to 2.4 ppm Cu | 6.0 | 6.0 | 6.0 |
| Example F Formulation diluted to 1.2 ppm Cu | — | — | — |
| Example G Formulation diluted to 1.2 ppm Cu | 5.3 | 6.0 | 6.0 |

The data in Table I indicate that after 5 minutes, the Example A Formulation log reduction value of 3.3 meets and exceeds the log reduction value for the chlorine standard at 30 seconds (value of 3.2). This indicates that the formulation given in Example A may be a strong candidate for replacing chlorine in swimming pool and spa use. Similarly, the data in Table II indicate that the formulations corresponding to Examples D, E, and G performed at least as well as the chlorine standard in the kill rates of *E. Coli* at 30 seconds. This indicates that the treatment agent formulations according to Examples D, E, and G may also be strong candidates for replacing chlorine and other treatment agents in water bodies. Example F was unstable and precipitated before testing. In addition, the treatment agent formulations of Examples A, D and G were diluted to copper levels of 1.2 ppm, a copper level below that accepted by the EPA for use in water consumed by humans. In any event, each of the formulations reduces or kills *E. Coli* in water bodies and may therefore be used as a treatment agent.

Although specific formulations are given as examples of the treatment agents disclosed by the present invention, it is understood that the present invention is not limited to such examples. Having thus described certain preferred embodiments of the present invention, it is to be understood that the invention is not to be limited by particular details set forth in the above description, as many apparent variations thereof are possible without departing from the spirit or scope of the present invention.

What is claimed is:

1. A water treatment agent, comprising:
   an amount of copper sulfate pentahydrate sufficient to provide algae control in a body of water to be treated;
   disodium ethylene diamine tetraacetic acid dihydrate;
   a scale inhibitor with the proviso that said scale inhibitor is not disodium ethylene diamine tetraacetic acid dihydrate; and
   a non-chlorine shocking agent that oxidizes organic matter in water.

2. The water treatment agent of claim 1, wherein said copper sulfate pentahydrate comprises between about 50 gm/liter and about 100 gm/liter copper sulfate pentahydrate in said water treatment agent.

3. The water treatment agent of claim 1, wherein said disodium ethylene diamine tetraacetic acid dihydrate comprises between about 4 gm/liter and about 8 gm/liter disodium ethylene diamine tetraacetic acid dihydrate in said water treatment agent.

4. The water treatment agent of claim 1, wherein the amount of said disodium ethylene diamine tetraacetic acid dihydrate in said water treatment agent does not exceed about 2.6 wt %.

5. The water treatment agent of claim 1, wherein said scale inhibitor comprises 1-hydroxyethylidene-1,1diphosphonic acid.

6. The water treatment agent of claim 1, wherein said scale inhibitor comprises between about 5 ml/liter and about 10 ml/liter 1-hydroxyethylidene-1,1-diphosphonic acid in said water treatment agent.

7. The water treatment agent of claim 1, wherein said shocking agent comprises monopotassium phosphate.

8. The water treatment agent of claim 1, wherein said shocking agent comprises between about 10 gm/liter and about 20 gm/liter monopotassium phosphate.

9. The water treatment agent of claim 1, wherein said shocking agent comprises potassium monopersulfate.

10. The water treatment agent of claim 1, wherein said shocking agent comprises between about 50 gm/liter and about 100 gm/liter potassium nionopersulfate.

11. The water treatment agent of claim 1, wherein said shocking agent is selected from the group consisting of monopotassium phosphate, potassium monopersulfate, sodium monopersulfate, alkali monopersulfates, and potassium hydrogen peroxymonosulfate sulfate.

12. The water treatment agent of claim 1, further comprising a buffering agent.

13. The water treatment agent of claim 12, wherein said buffering agent comprises monopotassium phosphate.

14. The water treatment agent of claim 12, wherein said buffering agent comprises sulfuric acid.

15. The water treatment agent of claim 12, wherein said buffering agent is selected from the group consisting of monopotassium phosphate, sulfuric acid, hydrochloric acid, nitric acid, muriatic acid, and oxalic acid.

16. The water treatment agent of claim 1, further comprising silver.

17. The water treatment agent of claim 16, wherein said silver comprises about 0.08 gm/liter silver nitrate in said water treatment agent.

18. The water treatment agent of claim 1, wherein the concentration of said copper sulfate pentahydrate in said water treatment agent does not exceed about 1.3 ppm.

19. A method of treating a body of water, comprising adding to said body of water an effective amount of the water treatment agent of claim 1.

20. The method of claim 19, further comprising establishing a pH of said body of water between a pH of about 5 and about 9 using a buffering agent prior to adding said water treatment agent to said body of water.

21. The method of claim 20, wherein said buffering agent is selected from the group consisting of monopotassium phosphate, sulfuric acid, hydrochloric acid, muriatic acid, and oxalic acid.

22. The method of claim 20, wherein said buffering agent comprises monopotassium phosphate in an amount sufficient to regulate the pH of said body of water between a pH of about 5 and about 9.

23. The method of claim 20, wherein said buffering agent comprises sulfuric acid in an amount sufficient to regulate the pH of said body of water between a pH of about 5 and about 9.

24. The method of claim 19, wherein said shocking agent is selected from the group consisting of monopotassium phosphate, potassium monopersulfate, sodium monopersulfate, alkali monopersulfates, and potassium hydrogen peroxymonosulfate sulfate.

25. The method of claim 19, wherein said adding of said water treatment agent to said body of water comprises adding said water treatment agent to said body of water to produce a copper concentration in said body of water between about 0.1 ppm copper and about 1.3 ppm copper.

26. The method of claim 19, wherein said 1-hydroxyethylidene-1,1-diphosphonic acid in said water treatment agent is in an amount sufficient to treat said body of water with between about 1 and about 10 ppm 1-hydroxyethylidene-1,1-diphosphonic acid.

27. The method of claim 19, wherein said copper sulfate pentahydrate in said water treatment agent does not exceed about 31.6 wt %.

28. An aqueous solution for treating water, comprising:

an amount of copper sulfate pentahydrate sufficient to provide algae control in a body of water to be treated;

disodium ethylene diamine tetraacetic acid dihydrate;

potassium monopersulfate;

1-hydroxyethylidene-1,1-diphosphonic acid;

about zero to about 15 wt % sulfuric acid; and about zero to about 33 wt % monopotassium phosphate;

wherein the amount of copper sulfate pentahydrate in said aqueous solution does not exceed about 31.6 wt %, the amount of disodium ethylene diamine tetraacetic acid dihydrate in said aqueous solution does not exceed about 2.56 wt %, the amount of potassium monopersulfate in said aqueous solution does not exceed about 8.6 wt %, and the amount of 1-hydroxyethylidene-1,1-diphosphonic acid in said aqueous solution does not exceed about 1 wt %.

29. A treatment agent for treating water, comprising:

an amount of copper sulfate pentahydrate sufficient to provide algae control in a body of water to be treated;

disodium ethylene diamine tetraacetic acid dihydrate;

potassium monopersulfate;

1-hydroxyethylidene-1,1-diphosphonic acid;

about zero to about 33 wt % monopotassium phosphate; and about zero to about 33 wt % sodium hydroxide;

wherein the amount of copper sulfate pentahydrate in said treatment agent does not exceed about 31.6 wt %, the amount of disodium ethylene diamine tetraacetic acid dihydrate in said treatment agent does not exceed about 2.56 wt %, the amount of potassium monopersulfate in said treatment agent does not exceed about 8.6 wt %, and the amount of 1-hydroxyethylidene-1,1-diphosphonic acid in said treatment agent does not exceed about 1 wt %.

30. The treatment agent of claim 29, comprising:

about 5 wt % copper sulfate pentahydrate;

about 0.8 wt % disodium ethylene diamine tetraacetic acid dihydrate;

potassium monopersulfate;

1-hydroxyethylidene-1,1-diphosphonic acid;

about 1 wt % monopotassium phosphate; and about 0.13 wt % sodium hydroxide;

wherein the amount of potassium monopersulfate in said treatment agent does not exceed about 8.6 wt %, and the amount of 1-hydroxyethylidene-1,1-diphosphonic acid in said treatment agent does not exceed about 1 wt %.

* * * * *